United States Patent
Kang

(10) Patent No.: US 9,258,493 B2
(45) Date of Patent: Feb. 9, 2016

(54) METHOD AND APPARATUS FOR RELAYING ULTRASOUND DATA

(71) Applicant: SAMSUNG MEDISON CO., LTD., Gangwon-do (KR)

(72) Inventor: Dae-woong Kang, Gangwon-do (KR)

(73) Assignee: SAMSUNG MEDISON CO., LTD., Hongcheon-gun, Gangwon-do (KR)

(*) Notice: Subject to any disclaimer, the term of this patent is extended or adjusted under 35 U.S.C. 154(b) by 560 days.

(21) Appl. No.: 13/717,500

(22) Filed: Dec. 17, 2012

(65) Prior Publication Data

US 2013/0215277 A1 Aug. 22, 2013

Related U.S. Application Data

(60) Provisional application No. 61/599,715, filed on Feb. 16, 2012.

(30) Foreign Application Priority Data

May 1, 2012 (KR) .................. 10-2012-0045987

(51) Int. Cl.
*H04N 5/30* (2006.01)
*G06F 19/00* (2011.01)

(52) U.S. Cl.
CPC .............. *H04N 5/30* (2013.01); *G06F 19/321* (2013.01)

(58) Field of Classification Search
None
See application file for complete search history.

(56) References Cited

U.S. PATENT DOCUMENTS

| 2002/0028995 | A1 | 3/2002 | Mault |
| 2007/0282201 | A1 | 12/2007 | Kim |
| 2009/0318808 | A1* | 12/2009 | Brader ................... 600/443 |
| 2011/0010192 | A1* | 1/2011 | Backhaus et al. ............. 705/2 |
| 2011/0087651 | A1* | 4/2011 | Westin et al. .............. 707/722 |

FOREIGN PATENT DOCUMENTS

| JP | 2004-265039 A | 9/2004 |
| KR | 10-2005-0093019 A | 9/2005 |
| KR | 10-2007-0107571 A | 11/2007 |
| KR | 10-2010-0036903 A | 4/2010 |
| KR | 10-2011-0014354 A | 2/2011 |
| KR | 10-2011-0093389 A | 8/2011 |
| KR | 10-2011-0122450 A | 11/2011 |
| KR | 2012-0009764 A | 2/2012 |
| WO | WO-2010-038918 A1 | 4/2010 |

OTHER PUBLICATIONS

Korean Office Action dated Aug. 27, 2014 issued in corresponding Korean Patent Application No. 10-2014-0063115 (English translation).

(Continued)

*Primary Examiner* — William C Vaughn, Jr.
*Assistant Examiner* — Eileen Adams
(74) *Attorney, Agent, or Firm* — McDermott Will & Emery LLP

(57) ABSTRACT

An ultrasound data relaying method is performed by an ultrasound data relaying apparatus. According to the method, user information is received from a mobile terminal connected to the ultrasound data relaying apparatus. Ultrasound photographing information is received from an ultrasound diagnosis apparatus. The ultrasound photographing information is transmitted to the mobile terminal based on the received user information.

18 Claims, 2 Drawing Sheets

(56) References Cited

OTHER PUBLICATIONS

Korean Office Action issued in Korean Application No. 10-2012-0045987 dated Mar. 26, 2014, w/English translation.
Notification of transmittal of the International Search Report and Written Opinion of the International Searching Authority, or the Declaration issued in PCT/KR2012/011439 dated Apr. 29, 2013.
Korean Notice of Non-Final Rejection, w/ English translation thereof, issued in Korean Patent Application No. 10-2012-0045987 dated Aug. 30, 2013.
Notice of Final Rejection dated Feb. 25, 2015 in Korean Patent Application No. 10-2014-63115 (English translation).
Korean final Office Action dated May 13, 2015 issued in Korean Patent No. 10-2014-63115 (English translation).

* cited by examiner

METHOD AND APPARATUS FOR RELAYING ULTRASOUND DATA

CROSS-REFERENCE TO RELATED PATENT APPLICATION

This U.S. non-provisional application claims benefit of the priority of U.S. Patent Provisional Application No. 61/599,715, filed on Feb. 16, 2012, in the U.S. Patent and Trademark Office, and benefit of the priority of Korean Patent Application No. 10-2012-0045987, filed on May 1, 2012, in the Korean Intellectual Property Office, the entire contents of which are hereby incorporated by reference.

TECHNICAL FIELD

The present inventive concept relates to a method and apparatus for relaying ultrasound data including an ultrasound image obtained by using an ultrasound diagnosis apparatus and additional information regarding the ultrasound image and transmitting the ultrasound data to a user's mobile terminal.

BACKGROUND

Ultrasound diagnosis apparatuses generate an ultrasound signal (generally greater than 20 kHz) to be transmitted to a predetermined part inside a target body by using a probe, and obtain an image of the part inside the target body by using information regarding a reflected echo signal. In particular, ultrasound diagnosis apparatuses are used for a medical purpose, such as a detection of impurities inside the target body, a measurement and observation of a wound of the target body, etc. Such ultrasound diagnosis apparatuses have various advantages in terms of real-time display and safety because there is no radioactive exposure compared to X-ray apparatuses. Thus, the ultrasound diagnosis apparatuses are commonly used together with other image diagnosis apparatuses.

An image (hereinafter referred to as an ultrasound image) obtained through ultrasound diagnosis apparatuses may be displayed on the ultrasound diagnosis apparatuses or may be stored in storage medium and displayed on other ultrasound diagnosis apparatuses. For example, the ultrasound image may be reduced and displayed on screens of cellular phones, portable electronic devices, personal digital assistant (PDAs), or tablet PCs, etc.

Digital Imaging and Communications in Medicine (DICOM) is a standard protocol in transmitting medical imaging and imaging information between medical devices. To share and transmit imaging information obtained through medical devices over a network, digitalization of the imaging information is essential. Thus, the importance of DICOM as the standard protocol for storing and transmitting medical imaging, is being emphasized.

SUMMARY

Aspects of the present inventive concept relate to a method and apparatus for efficiently relaying ultrasound data including an ultrasound image obtained by using an ultrasound diagnosis apparatus to a user's mobile terminal, and a computer readable recording medium storing a program for executing the method.

An aspect of the present inventive concept encompasses an ultrasound data relaying method, performed by an ultrasound data relaying apparatus, may include: receiving user information from a mobile terminal connected to the ultrasound data relaying apparatus; receiving ultrasound photographing information from an ultrasound diagnosis apparatus; and transmitting the ultrasound photographing information to the mobile terminal corresponding to the received user information.

The user information may include at least one of an identification (ID) number of the mobile terminal, a user ID of the mobile terminal, and a name of a fetus.

The user information may be received from the mobile terminal through an application installed in the mobile terminal.

The ultrasound photographing information may include at least one of an ultrasound image of a target obtained by the ultrasound diagnosis apparatus, Doppler sound of the target, measurement information indicating a size or length of the target, and comparison information that is a result obtained by comparing the measurement information with a previously determined average value.

The receiving of the ultrasound photographing information may include: receiving at least one of the ultrasound photographing information and additional information relating to the ultrasound photographing information. The transmitting may include: transmitting at least one of the ultrasound photographing information and the additional information.

The additional information may include at least one of clinic information of a clinic in which photographing is performed by using the ultrasound diagnosis apparatus, reservation information of a user identified based on the user information, and diagnosis history information of the user identified based on the user information.

The ultrasound photographing information may be accumulated and stored in an external server, wherein the receiving of the ultrasound photographing information includes: receiving the ultrasound photographing information transmitted from the external server to the ultrasound diagnosis apparatus.

The ultrasound data relaying method may further include transmitting the ultrasound photographing information to a plurality of mobile terminals corresponding to the received user information. The received user information may include identification information of the plurality of mobile terminals.

Another aspect of the present inventive concept relates to an ultrasound data relaying method, performed by an ultrasound data relaying apparatus, including: receiving user information from a mobile terminal connected to the ultrasound data relaying apparatus; receiving ultrasound photographing information from an external server; and transmitting the ultrasound photographing information to the mobile terminal corresponding to the received user information.

The ultrasound photographing information may follow the Digital Imaging and Communications in Medicine (DICOM) standard.

Still another aspect of the present inventive concept encompasses an ultrasound data relaying apparatus including: a user information receiving unit configured to receive user information from a mobile terminal connected to the ultrasound data relaying apparatus; a photographing information receiving unit configured to receive ultrasound photographing information from an ultrasound diagnosis apparatus; a transmitting unit configured to transmit the ultrasound photographing information to the mobile terminal corresponding to the received user information; and a control unit for configured to control the user information receiving unit, the photographing information receiving unit, and the transmitting unit.

Further another aspect of the present inventive concept relates to an ultrasound data relaying apparatus including: a user information receiving unit configured to receive user information from a mobile terminal connected to the ultrasound data relaying apparatus; a photographing information receiving unit configured to receive ultrasound photographing information from an external server; a transmitting unit configured to transmit the ultrasound photographing information to the mobile terminal corresponding to the received user information; and a control unit configured to control the user information receiving unit, the photographing information receiving unit, and the transmitting unit.

Another aspect of the present inventive concept relates to a computer readable recording medium having embodied thereon a computer program for executing the ultrasound image data providing method.

BRIEF DESCRIPTION OF THE DRAWINGS

The foregoing and other features of the inventive concept will be apparent from more particular description of embodiments of the inventive concept, as illustrated in the accompanying drawings in which like reference characters may refer to the same or similar parts throughout the different views. The drawings are not necessarily to scale, emphasis instead being placed upon illustrating the principles of the embodiments of the inventive concept.

DETAILED DESCRIPTION OF THE EMBODIMENTS

Figure 1:
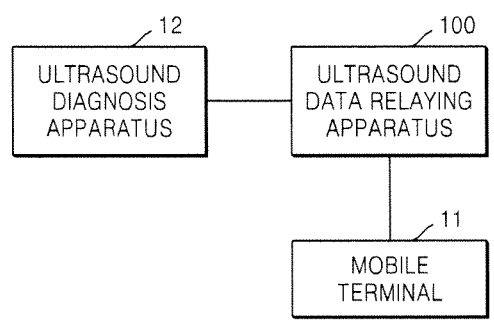
FIG. 1 is a block diagram of an ultrasound system according to embodiments of the present inventive concept.

Exemplary embodiments of the inventive concept will be described below in more detail with reference to the accompanying drawings. The embodiments of the inventive concept may, however, be embodied in different forms and should not be construed as limited to the embodiments set forth herein. Like reference numerals may refer to like elements throughout the specification.

Most of the terms used herein are general terms that have been widely used in the technical art to which the present inventive concept pertains. However, some of the terms used herein may be created reflecting intentions of technicians in this art, precedents, or new technologies. Also, some of the terms used herein may be arbitrarily chosen by the present applicant. In this case, these terms are defined in detail below. Accordingly, the specific terms used herein should be understood based on the unique meanings thereof and the whole context of the present inventive concept.

In the present disclosure, it should be understood that the terms, such as 'including' or 'having,' etc., are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added. Also, the terms, such as 'unit' or 'module', etc., should be understood as a unit that processes at least one function or operation and that may be embodied in a hardware manner, a software manner, or a combination of the hardware manner and the software manner. As used herein, the term "and/or" includes any and all combinations of one or more of the associated listed items. Expressions such as "at least one of," when preceding a list of elements, modify the entire list of elements and do not modify the individual elements of the list.

The embodiments of the present inventive concept will now be described more fully with reference to the accompanying drawings.

FIG. 1 is a block diagram of an ultrasound system according to an embodiment of the present inventive concept.

Referring to FIG. 1, the ultrasound system may include an ultrasound data relaying apparatus 100, a mobile terminal 11, and an ultrasound diagnosis apparatus 12. The ultrasound system may further include other elements besides the elements shown in FIG. 1.

The ultrasound data relaying apparatus 100 relays ultrasound data between the ultrasound diagnosis apparatus 12 and the mobile terminal 11. More particularly, the ultrasound data relaying apparatus 100 may receive user information from the mobile terminal 11 connected thereto, receive ultrasound photographing information from the ultrasound diagnosis apparatus 12, and transmit the ultrasound photographing information to the mobile terminal 11 corresponding to the received user information.

The ultrasound data relaying apparatus 100 may be any devices configured to receive, transmit, and relay the ultrasound data. According to an embodiment of the present inventive concept, the ultrasound data relaying apparatus 100 may be a Digital Imaging and Communications in Medicine (DICOM) gateway. A detailed construction of the ultrasound data relaying apparatus 100 will be described with reference to FIG. 2.

The mobile terminal 11 transmits the user information to the ultrasound data relaying apparatus 100 and receives the ultrasound data from the ultrasound data relaying apparatus 100. Examples of the mobile terminal 11 may include a laptop computer, a personal digital assistant (PDA), a tablet PC, a cellular phone, a smartphone, etc. The smartphone may be a mobile phone built on a mobile operating system, thereby enabling to download and install an application relating to the present inventive concept into the smartphone. In addition, various types of devices may correspond to the mobile terminal 11. The mobile terminal 11 may be connected to the ultrasound data relaying apparatus 100 by wire or wirelessly to transmit the user information and receive the ultrasound data. In a case where the ultrasound data relaying apparatus 100 and the mobile terminal 11 are connected to each other wirelessly, a communication technology such as Wi-Fi, 3G, IEEE 802.16e (mobile WiMAX, e.g., WiBro [trade]), Long Term Evolution (LTE), Bluetooth, etc. may be utilized. However, it will be understood by those of ordinary skill in the art that the present inventive concept is not limited thereto and other numerous communication technologies may be utilized.

The user information transmitted by the mobile terminal 11 may include at least one of an identification (ID) number of the mobile terminal 11, a user ID of the mobile terminal 11, and a name of a fetus. The ID number of the mobile terminal 11 may be, for example, when the mobile terminal 11 is a cellular phone, a cellular phone number or a four-digit number of the cellular phone number. The user ID of the mobile terminal 11 may be a combination of text and/or numbers optionally set by the user of the mobile terminal 11. The name of the fetus is a name called by a mother before the fetus is born and may be included in the user information. The user information may be used by the ultrasound data relaying apparatus 100 to identify the mobile terminal 11 and determine a target to which the ultrasound data is transmitted.

The user information may be also received from the mobile terminal 11 through an application installed in the mobile terminal 11. The mobile terminal 11 may be connected to the ultrasound data relaying apparatus 100 by wire or wirelessly, and, according to an embodiment of the present inventive concept, may be connected to the ultrasound data relaying apparatus 100 via a universal serial bus (USB).

To explain a case where the mobile terminal 11 is a smartphone, the user of the mobile terminal 11 may download and install an application relating to the present inventive concept. Thereafter, the user of the smartphone may connect the smartphone to the ultrasound data relaying apparatus 100 by wire, e.g., using a USB cable, or wirelessly, execute the application installed in the smartphone, and input the user information. The user information inputted into the smartphone may be transmitted to the ultrasound data relaying apparatus 100 so that the ultrasound data relaying apparatus 100 may identify the smartphone based on the user information.

Thereafter, the ultrasound data relaying apparatus 100 may transmit the ultrasound data received from the ultrasound diagnosis apparatus 12 to the smartphone by wire or wirelessly. The received ultrasound data may be directly displayed through the application installed in the smartphone.

The ultrasound diagnosis apparatus 12 transmits the ultrasound data to the ultrasound data relaying apparatus 100. The ultrasound data transmitted by the ultrasound diagnosis apparatus 12 may include one of ultrasound photographing information and additional information relating to the ultrasound photographing information. The ultrasound photographing information may include at least one of an ultrasound image of a target obtained by the ultrasound diagnosis apparatus 12, Doppler sound of the target, measurement information indicating a size or length of the target, and comparison information that is a result obtained by comparing the measurement information with a previously determined average value. The ultrasound photographing information will now be described in detail.

The ultrasound diagnosis apparatus 12 may scan the target by using a probe and obtain the ultrasound image. The ultrasound image obtained by the ultrasound diagnosis apparatus 12 may be a 2D image of the target or 3D volume data thereof. The target scanned by the ultrasound diagnosis apparatus 12 may be a mother who is pregnant with a fetus, or the fetus, but not limited thereto.

The ultrasound diagnosis apparatus 12 may also obtain the Doppler sound measured from the target. Furthermore, the ultrasound diagnosis apparatus 12 may transmit the Doppler sound that is sound information along with the obtained ultrasound image to the ultrasound data relaying apparatus 100.

The ultrasound diagnosis apparatus 12 may also perform a measuring operation on a specific part of the target from the obtained ultrasound image. For example, in a case where the ultrasound diagnosis apparatus 12 obtains an ultrasound image of the fetus, the ultrasound diagnosis apparatus 12 may measure a thickness of nuchal translucency (NT) or a crown rump length (CRL) of the fetus from the ultrasound image of the fetus.

Furthermore, the ultrasound diagnosis apparatus 12 may perform a comparing operation which compares a result of the measuring operation with a previously determined average value of a specific part of the fetus.

For example, in a case where the ultrasound diagnosis apparatus 12 obtains the ultrasound image of the fetus, the ultrasound diagnosis apparatus 12 may previously store an average value of the specific part of the fetus with respect to a pregnancy period. Accordingly, the ultrasound diagnosis apparatus 12 may compare the result of the measurement operation with the previously determined average value and determine whether the CRL of the fetus is greater or smaller than the average value with respect to the pregnancy period. Alternatively, the ultrasound diagnosis apparatus 12 may compare the result of the measurement operation with the average value and estimate the pregnancy period based on a comparison result. That is, the ultrasound diagnosis apparatus 12 may compare the CRL of the fetus with average value and estimate the current pregnancy period.

The additional information transmitted by the ultrasound diagnosis apparatus 12 may include at least one of clinic information of a clinic in which photographing is performed by using the ultrasound diagnosis apparatus 12, reservation information of a user identified based on the user information, and diagnosis history information of the user identified based on the user information. The ultrasound data relaying apparatus 100 may transmit the received additional information to the mobile terminal 11. Each piece of the additional information will now be described in detail.

The clinic information may include various pieces of information regarding the clinic in which an operation of photographing the target is performed by using the ultrasound diagnosis apparatus 12. That is, the clinic information may be various pieces of information regarding the clinic equipped with the ultrasound diagnosis apparatus 12. The clinic information may include a name of the clinic, a phone number thereof, an address thereof, etc.

The reservation information may include a treatment date, a treatment time, information regarding a doctor-in-charge, etc. reserved in a corresponding clinic with regard to the user of the mobile terminal 11 identified based on the user information. The diagnosis history information may include information regarding a result of photographing performed by the user of the mobile terminal 11 identified based on the user information before corresponding photographing is performed. That is, for example, when the ultrasound diagnosis apparatus 12 obtains ultrasound data of the fetus, the ultrasound data relaying apparatus 100 may transmit ultrasound photographing information of the fetus photographed one month ago to the mobile terminal 11, in addition to current ultrasound photographing information of the fetus.

The ultrasound data transmitted by the ultrasound diagnosis apparatus 12 may be data stored in the ultrasound diagnosis apparatus 12, whereas the ultrasound data may be stored in an external server (not separately shown) other than the ultrasound diagnosis apparatus 12. That is, the ultrasound data including the ultrasound photographing information may be accumulated and stored in a clinic server and transmitted to the ultrasound diagnosis apparatus 12 according to a signal received from the ultrasound diagnosis apparatus 12. Thereafter, the ultrasound diagnosis apparatus 12 may transmit the ultrasound data received from the external server to the ultrasound data relaying apparatus 100. In particular, a Picture Archiving and Communication System (PACS) may store the ultrasound data in the external server and transmit the ultrasound data to the ultrasound data relaying apparatus 100 through the ultrasound diagnosis apparatus 12.

According to another embodiment of the present inventive concept, the ultrasound data stored in the external server may be transmitted to the ultrasound data relaying apparatus 100 without going through the ultrasound diagnosis apparatus 12.

For example, in a case where the ultrasound data is stored in the external server, the external server may directly transmit the ultrasound data to the ultrasound data relaying apparatus 100 by wire or wirelessly according to the signal received from the ultrasound diagnosis apparatus 12.

According to another embodiment of the present inventive concept, the ultrasound data transmitted by the ultrasound diagnosis apparatus 12 may be data following the DICOM standard and may be transmitted based on the DICOM standard. As described above, the DICOM standard is a communication standard between medical devices.

Figure 2:
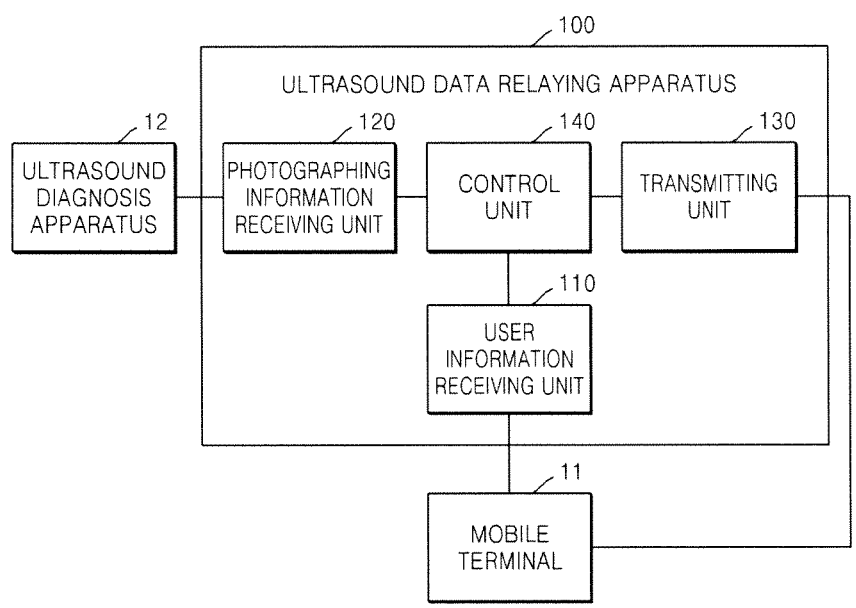
FIG. 2 is a block diagram of an ultrasound data relaying apparatus according to an embodiment of the present inventive concept.

FIG. 2 is a block diagram of the ultrasound data relaying apparatus 100 according to an embodiment of the present inventive concept.

Referring to FIG. 2, the ultrasound data relaying apparatus 100 according to an embodiment of the present inventive concept may include a user information receiving unit 110, a photographing information receiving unit 120, a transmitting unit 130, and a control unit 140.

Elements of the ultrasound data relaying apparatus 100 related to an embodiment of the present inventive concept are illustrated in FIG. 2. However, it will be understood by those of ordinary skill in the art that besides the elements of the ultrasound data relaying apparatus 100 illustrated in FIG. 2 other elements may be further included.

The user information receiving unit 110 receives user information from the mobile terminal 11 connected to the ultrasound data relaying apparatus 100. The user information received by the user information receiving unit 110 may include at least one of an ID number of the mobile terminal 11, a user ID of the mobile terminal 11, and a name of a fetus. The user information receiving unit 110 may receive the user information from the mobile terminal 11 connected to the ultrasound data relaying apparatus 100 by wire or wirelessly based on a previously determined standard. The user information received by the user information receiving unit 110 is described in detail with reference to FIG. 1, and thus a detailed description thereof is omitted here.

According to an embodiment of the present inventive concept, the user information received by the user information receiving unit 110 may be displayed on a screen of the ultrasound data relaying apparatus 100. That is, a user of the ultrasound data relaying apparatus 100 may identify a user of the mobile terminal 11 by using the user information displayed on the screen of the ultrasound data relaying apparatus 100.

According to another embodiment of the present inventive concept, the user information receiving unit 110 may transmit the received user information to an authentication unit (not separately shown). Accordingly, the authentication unit (not separately shown) may compare user information stored in an external server (not separately shown) with the user information received by the user information receiving unit 110 and authenticate the user of the mobile terminal 11 currently connected to the ultrasound data relaying apparatus 100.

The photographing information receiving unit 120 receives ultrasound photographing information from the ultrasound diagnosis apparatus 12. The ultrasound photographing information received by the photographing information receiving unit 120 may include at least one of an ultrasound image of a target, Doppler sound of the target, measurement information of the target, and comparison information obtained based on the measurement information as previously described with reference to FIG. 1. The photographing information receiving unit 120 may receive the ultrasound photographing information based on the DICOM standard.

According to an embodiment of the present inventive concept, the photographing information receiving unit 120 may receive at least one of the ultrasound photographing information and additional information relating to the ultrasound photographing information. The additional information may include at least one of clinic information, reservation information, and diagnosis history information as described above.

Although the photographing information receiving unit 120 may generally receive the ultrasound photographing information from the ultrasound diagnosis apparatus 12 by wire, the present inventive concept is not limited thereto, and various wireless communication methods described above may be used to receive the ultrasound photographing information. Also, according to an embodiment of the present inventive concept, the photographing information receiving unit 120 may receive the ultrasound photographing information from an external server (not separately shown) other than the ultrasound diagnosis apparatus 12.

The transmitting unit 130 transmits the ultrasound photographing information to the mobile terminal 11 corresponding to the received user information. According to the embodiment of the present inventive concept described above, the transmitting unit 130 may transmit at least one of the ultrasound photographing information and the additional information to the mobile terminal 11 corresponding to the received user information. The transmitting unit 130 may also transmit ultrasound data to the mobile terminal 11 by wire or wirelessly.

The mobile terminal 11 to which the transmitting unit 130 transmits the ultrasound photographing information may be determined as a destination based on the user information received by the user information receiving unit 110. That is, the transmitting unit 130 usually transmits the ultrasound photographing information to the mobile terminal 11 that has previously transmitted the user information to the user information receiving unit 110. However, in a case where information regarding a particular mobile terminal, which is not the mobile terminal 11 and to which the ultrasound photographing information is to be transmitted, is included in the user information transmitted by the mobile terminal 11, the transmitting unit 130 may transmit the ultrasound photographing information to the particular mobile terminal. This will be described in detail with reference to FIG. 3.

The control unit 140 generally controls operations of the user information receiving unit 110, the photographing information receiving unit 120, and the transmitting unit 130. The control unit 140 may control elements that may be included in the ultrasound data relaying apparatus 100 besides the elements shown in FIG. 2. The control unit 140 may include a central processing unit, a microprocessor and a graphic processing unit, and the like.

Figure 3:
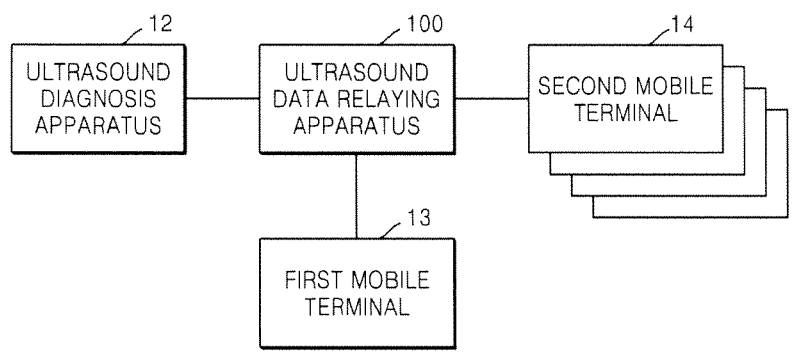
FIG. 3 is a block diagram for describing a transmission of ultrasound data to a mobile terminal other than a mobile terminal that transmits user information according to an embodiment of the present inventive concept.

FIG. 3 is a block diagram for describing a transmission of ultrasound data to a second mobile terminal 14 other than a first mobile terminal 13 that transmits user information according to an embodiment of the present inventive concept. The ultrasound data relaying apparatus 100 may include the user information receiving unit 110, the photographing information receiving unit 120, the transmitting unit 130, and the control unit 140 that are described above with reference to FIG. 2.

According to the present embodiment of the present inventive concept, the user information receiving unit 110 may receive the user information from the first mobile terminal 13. The photographing information receiving unit 120 may receive ultrasound photographing information from the ultrasound diagnosis apparatus 12. The photographing information receiving unit 120 may receive at least one of the ultrasound photographing information and additional information from the ultrasound diagnosis apparatus 12.

Thereafter, the transmitting unit 130 may transmit ultrasound photographing information to the second mobile terminal 14 corresponding to the received user information. That is, in a case where the user information received from the first mobile terminal 13 includes information regarding the second mobile terminal 14 that is to share the ultrasound photographing information, the transmitting unit 130 may transmit the ultrasound photographing information to the second mobile terminal 14 based on the user information. The second mobile terminal 14 may include a plurality of mobile terminals. The second mobile terminal 14 may also include the first mobile terminal 13.

For example, in a case where the photographing information receiving unit 120 receives ultrasound photographing information of a fetus from the ultrasound diagnosis apparatus 12, the first mobile terminal 13 may be a cellular phone of the mother of the fetus. In this regard, the user information to be transmitted by the first mobile terminal 13 may include a mother's cellular phone number, a mother's husband's cellular phone number, and mother's family members' cellular phone numbers as information regarding the second mobile terminal 14.

More specifically, in a case where a plurality of users are to receive the ultrasound photographing information of the fetus, the user information to be received by the user information receiving unit 110 may include information regarding each of the users' mobile terminals that are to share the ultrasound photographing information as information regarding a plurality of second mobile terminals 14.

The control unit 140 may transmit the information regarding the plurality of second mobile terminals 14 included in the user information received by the user information receiving unit 110 to the transmitting unit 130. Thereafter, the transmitting unit 130 may transmit the ultrasound photographing information to the plurality of second mobile terminals 14 based on the user information.

An ultrasound data relaying method using the construction of the ultrasound data relaying apparatus 100 will now be described with reference to FIG. 4.

Figure 4:
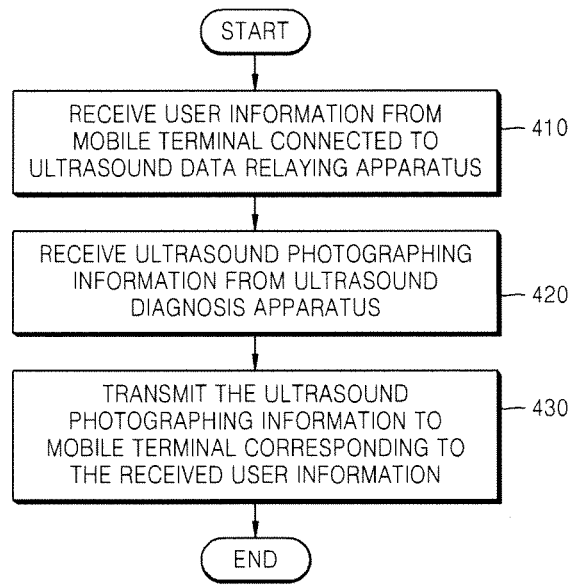
FIG. 4 is a flowchart illustrating an ultrasound data relaying method according to an embodiment of the present inventive concept.

FIG. 4 is a flowchart illustrating an ultrasound data relaying method according to an embodiment of the present inventive concept. The method shown in FIG. 4 includes operations time-sequentially performed by the ultrasound data relaying apparatus 100 of FIG. 1, the user information receiving unit 110, the photographing information receiving unit 120, the transmitting unit 130, and the control unit 140. Thus, although omitted below, the descriptions of the elements of FIGS. 1 through 3 may also apply to the method illustrated in FIG. 4.

In operation 410, user information is received from a mobile terminal connected to an ultrasound data relaying apparatus. The user information may include at least one of an ID number of the mobile terminal, a user ID of the mobile terminal, a name of a fetus, and information regarding a plurality of mobile terminals. The user information may be received by wire or wirelessly. The user information received in operation 410 may be transmitted to a control unit.

In operation 420, ultrasound photographing information is received from an ultrasound diagnosis apparatus. The ultrasound photographing information may include at least one of an ultrasound image of a target obtained by the ultrasound diagnosis apparatus, Doppler sound of the target, measurement information indicating a size or length of the target, and comparison information that is a result obtained by comparing the measurement information with an average value. The ultrasound photographing information may follow the DICOM standard and may be received by wire or wirelessly.

According to an embodiment of the present inventive concept, in operation 420, at least one of the ultrasound photographing information and additional information relating to the ultrasound photographing information may be received. The additional information may include at least one of clinic information, reservation information of a user identified by using the user information, and diagnosis history information of the user identified by using the user information.

In operation 430, the ultrasound photographing information may be transmitted to the mobile terminal corresponding to the received user information. In a case where the received user information includes the information regarding the plurality of mobile terminals, the ultrasound photographing information may be transmitted to the plurality of mobile terminals. In this regard, the plurality of mobile terminals may include the mobile terminal that transmits the user information.

According to an embodiment of the present inventive concept, in operation 430, at least one of the ultrasound photographing information and the additional information may be transmitted to the mobile terminal corresponding to the received user information.

The embodiments of the present inventive concept may be written as computer programs and can be implemented in general-use digital computers that execute the programs using a computer readable recording medium. In addition, a structure of data used in the above-described method may be recorded in a computer readable recording medium through various methods. Examples of the computer readable recording medium include magnetic storage media (e.g., Read-only Memories (ROMs), Random Access Memories (RAMs), universal serial buses (USBs), floppy disks, hard disks, etc.), optical recording media (e.g., CD-ROMs, or DVDs), and storage media such as PC interfaces (e.g., Peripheral Component Interconnect (PCI), PCI-express, WiFi, etc.).

According to the descriptions provided above with reference to FIGS. 1 through 4, ultrasound data is efficiently shared between an ultrasound diagnosis apparatus and one or more mobile terminals. Even if no software or hardware is installed in the ultrasound diagnosis apparatus, the above-described method, apparatus, and computer readable recording medium may be used to conveniently relay and share the ultrasound data.

As described above, an ultrasound image of a fetus obtained through an ultrasound diagnosis apparatus can be efficiently transmitted to mobile terminals owned by persons who are interested in information regarding the fetus by using an apparatus for relaying ultrasound data. Further, the ultrasound data can be conveniently transmitted to mobile terminals by using the apparatus for relaying ultrasound data even if no software or hardware is installed in the ultrasound diagnosis apparatus.

While the present inventive concept has been particularly shown and described with reference to exemplary embodiments thereof, it will be understood by those of ordinary skill in the art that various changes in form and details may be made therein without departing from the spirit and scope of the present inventive concept as defined by the following claims.

What is claimed is:

1. An ultrasound data relaying method, performed by an ultrasound data relaying apparatus, the method comprising steps of:

receiving, by the ultrasound data relaying apparatus connected to an ultrasound diagnosis apparatus and a mobile terminal by wire or wirelessly, user information comprising an identification number of the mobile terminal from the mobile terminal through an application installed in the mobile terminal;

receiving ultrasound photographing information comprising an ultrasound image of a target obtained by the ultrasound diagnosis apparatus and measurement information indicating at least one of a size and length of the target from the ultrasound diagnosis apparatus; and transmitting the ultrasound photographing information comprising the ultrasound image and the measurement information indicating the at least one of a size and length of the target to the mobile terminal corresponding to the received user information.

2. The method of claim 1, wherein the user information further comprises at least one of a user ID of the mobile terminal and a name of a fetus.

3. The method of claim 1, wherein the ultrasound photographing information further comprises at least one of Doppler sound of the target and comparison information that is a result obtained by comparing the measurement information with a previously determined average value.

4. The method of claim 1, wherein:
the step of receiving the ultrasound photographing information comprises the step of: receiving at least one of the ultrasound photographing information and additional information relating to the ultrasound photographing information, and
the step of transmitting comprises the step of: transmitting at least one of the ultrasound photographing information and the additional information.

5. The method of claim 4, wherein the additional information comprises at least one of clinic information of a clinic in which photographing is performed by using the ultrasound diagnosis apparatus, reservation information of a user identified based on the user information, and diagnosis history information of the user identified based on the user information.

6. The method of claim 1, wherein:
the ultrasound photographing information is accumulated and stored in an external server, and
the step of receiving the ultrasound photographing information comprises the step of: receiving the ultrasound photographing information transmitted from the external server to the ultrasound diagnosis apparatus.

7. The method of claim 1, further comprising steps of:
receiving the ultrasound photographing information from an external server; and
transmitting the ultrasound photographing information to the mobile terminal corresponding to the received user information.

8. The method of claim 1, wherein the ultrasound photographing information follows the Digital Imaging and Communications in Medicine (DICOM) standard.

9. A non-transitory computer readable recording medium storing a program for executing the steps of the ultrasound data relaying method of claim 1.

10. The method of claim 1, further comprising:
transmitting the ultrasound photographing information to a plurality of mobile terminals corresponding to the received user information,
wherein the received user information comprises identification information of the plurality of mobile terminals.

11. An ultrasound data relaying apparatus, comprising:
a user information receiving unit configured to receive user information comprising an identification number of the mobile terminal from the mobile terminal through an application installed in the mobile terminal;
a photographing information receiving unit configured to receive ultrasound photographing information comprising an ultrasound image of a target obtained by the ultrasound diagnosis apparatus and measurement information indicating at least one of a size and length of the target from the ultrasound diagnosis apparatus;
a transmitting unit configure to transmit the ultrasound photographing information comprising the ultrasound image and the measurement information indicating the at least one of a size and length of the target to the mobile terminal corresponding to the received user information; and
a control unit configured to control the user information receiving unit, the photographing information receiving unit, and the transmitting unit,
wherein the ultrasound data relaying apparatus is connected to the ultrasound diagnosis apparatus and the mobile terminal by wire or wirelessly.

12. The apparatus of claim 11, wherein the user information further comprises at least one of a user ID of the mobile terminal and a name of a fetus.

13. The apparatus of claim 11, wherein the ultrasound photographing information further comprises at least one of Doppler sound of the target and comparison information that is a result obtained by comparing the measurement information with a previously determined average value.

14. The apparatus of claim 11, wherein:
the photographing information receiving unit receives at least one of the ultrasound photographing information and additional information relating to the ultrasound photographing information, and
the transmitting unit transmits at least one of the ultrasound photographing information and the additional information.

15. The apparatus of claim 14, wherein the additional information comprises at least one of clinic information of a clinic in which photographing is performed by using the ultrasound diagnosis apparatus, reservation information of a user identified based on the user information, and diagnosis history information of the user identified based on the user information.

16. The apparatus of claim 11, wherein:
the ultrasound photographing information is accumulated and stored in an external server, and
the photographing information receiving unit receives the ultrasound photographing information from the external server.

17. The apparatus of claim 11, wherein the ultrasound photographing information follows the DICOM standard.

18. An ultrasound data relaying apparatus, comprising:
a user information receiving unit configured to receive user information comprising an identification number of the mobile terminal from the mobile terminal through an application installed in the mobile terminal;
a photographing information receiving unit configured to receive ultrasound photographing information comprising an ultrasound image of a target obtained by an ultrasound diagnosis apparatus and measurement information indicating at least one of a size and length of the target from the external server;
a transmitting unit configured to transmit the ultrasound photographing information comprising the ultrasound image and the measurement information indicating the at least one of a size and length of the target to the mobile terminal corresponding to the received user information; and a control unit configured to control the user information receiving unit, the photographing information receiving unit, and the transmitting unit, wherein the ultrasound data relaying apparatus is connected to the mobile terminal and the external server by wire or wirelessly.

\* \* \* \* \*